United States Patent [19]

Snell et al.

[11] Patent Number: 4,791,936

[45] Date of Patent: * Dec. 20, 1988

[54] APPARATUS FOR INTERPRETING AND DISPLAYING CARDIAC EVENTS OF A HEART CONNECTED TO A CARDIAC PACING MEANS

[75] Inventors: Jeffery D. Snell, Northridge; Brian M. Mann, Los Angeles; Jason A. Sholder, Canoga Park, all of Calif.

[73] Assignee: Siemens-Pacesetter, Inc., Sylmar, Calif.

[*] Notice: The portion of the term of this patent subsequent to Jun. 24, 2003 has been disclaimed.

[21] Appl. No.: 876,612

[22] Filed: Jun. 20, 1986

Related U.S. Application Data

[63] Continuation-in-part of Ser. No. 701,795, Feb. 15, 1985, Pat. No. 4,596,255, which is a continuation of Ser. No. 440,149, Nov. 8, 1982, abandoned.

[51] Int. Cl.[4] .................................................. A61B 5/04
[52] U.S. Cl. .............................. 128/697; 128/419 PT
[58] Field of Search ................. 128/696, 419 PT, 903, 128/697, 702, 712; 340/870.01, 870.18, 870.26

[56] References Cited

U.S. PATENT DOCUMENTS

| | | | |
|---|---|---|---|
| 3,782,367 | 1/1974 | Hochberg et al. | 128/206 A |
| 3,952,750 | 4/1976 | Mirowski et al. | 128/419 D |
| 4,098,267 | 7/1978 | Stein et al. | 128/206 G |
| 4,142,533 | 3/1979 | Brownlee et al. | 128/419 PT |
| 4,193,393 | 3/1980 | Schlager | 128/710 |
| 4,232,679 | 11/1980 | Schulman | 128/419 PG |
| 4,281,664 | 8/1981 | Duggan | 128/696 |
| 4,374,382 | 2/1983 | Markowitz | 128/419 P |
| 4,596,255 | 6/1986 | Snell et al. | 128/697 |

OTHER PUBLICATIONS

Mancini et al., "IEEE Transactions on Biomedical Engineering," vol. 22, No. 4, Jul. 1975, pp. 281-286.

Primary Examiner—Francis J. Jaworski
Assistant Examiner—George Manuel
Attorney, Agent, or Firm—Bryant R. Gold

[57] ABSTRACT

An apparatus for interpreting and displaying cardiac events of a heart connected to an implanted cardiac pacing means (2) is disclosed. The apparatus includes a telemetry head (4), at least one interpreting means (6), and a controller (14). Information telemetered from the implanted pacing means is separated into identifiable sets of data pertaining to prescribed functions, such as atrial events, ventricular events, pacemaker timed events, sensor events, and the like. Skin ECG information may also be received through another interpreting means (12) in addition to pacemaker telemetered data. Parallel processing channels are employed to process all the received data while maintaining synchronization therebetween. Memory means (16) allow the synchronized processed data to be stored for subsequent print out through a D/A converter (20) and printer (22), or to be displayed on a display monitor (26). The display monitor is controlled by display logic (24) that includes the capability to simultaneously display a plurality of selected data sets while maintaining the synchronization therebetween, and that further allows displayed events to be identified with unique markers (44, 46, 64, 66) or synchronized with displayed time intervals (82, 84, 92, 94) associated with the operation of the pacemaker.

17 Claims, 3 Drawing Sheets

APPARATUS FOR INTERPRETING AND DISPLAYING CARDIAC EVENTS OF A HEART CONNECTED TO A CARDIAC PACING MEANS

This application is a continuation-in-part of application Ser. No. 701,795, filed 02/15/85, now issued as U.S. Pat. No. 4,596,255 which was a continuation of application Ser. No. 440,149 filed 11/8/82, now abandoned.

The present invention relates to devices or apparatus which are capable of receiving telemetric signals from an implanted cardiac pacemaker and signals from ECG electrodes connected to the skin of an individual to provide a visual display representative of the cardiac events as seen by the cardiac pacemaker and a skin ECG wave pattern synchronized in real time. Further, the invention relates to any field of diagnostic apparatus which can be used for interpreting the activities of a heart connected to a cardiac pacing apparatus.

BACKGROUND OF THE INVENTION

In the past, there have been significant breakthroughs in the development of cardiac pacemakers. Such cardiac pacemakers are ones which are programmable and can pace in a variety of pacing modes. For example, pacemakers can pace in VOO, VVI, VVT, AOO, AAI, AAT, DOO, DVI and DDD modes. Such new and innovative pacemakers come close to simulating the ultimate physiological pacing apparatus. However, there still exists a great difficulty in determining how a particular implanted pacing apparatus is functioning at any given point in time.

A great majority of diagnostic tools used to evaluate the performance of a cardiac pacemaker have been subordinated to activity not seen in real time. That is, such evaluation typically requires the production of ECG tapes created by connecting the individual having the implanted pacing apparatus to a series of electrodes so that the ECG tape could be made. After this tape is made, the physician or other technical person views the tape using calipers. This inspection determines whether the proper pacing scheme was accomplished for the individual having the implanted pacing apparatus (or pacemaker).

In most cases in the past, this evaluation did not take place in real time. It could be hours, days, or even weeks before a proper evaluation could be made as to whether proper pacing was taking place. There has not been any attempt to develop a diagnostic tool which could display a visual representation of the actual pacemaker activity and its associated ECG wave pattern in real time. The major problem in development of such a diagnostic apparatus was centered on the lack of the ability to provide visual representations of sequential cardiac events as seen by the pacing apparatus.

In the past, there have been futile attempts to provide outputs from the pacing apparatus as to mark cardiac events. The events that could not be effectively marked were outputs from the pacer to indicate an atrial or ventricular pulse to cause a depolarization of the cardiac chambers or when the pacing apparatus senses a natural P-wave or R-wave. There were no devices which over a long period of time could actually provide information indicative of the complete sequence of cardiac events as seen by the pacer.

Coupled with the problems identified in the foregoing paragraphs, there have also been additional problems in determining whether the pacemaker was performing in a manner such that there were proper refractory periods following depolarization of the atrium or ventricle. In cases when the natural refractory period of the heart was not long enough to mask the next cardiac event, such as a retrograde R-wave causing depolarization of the atrium, it was not desirable for such a cardiac event to be detected by the pacing apparatus. In these situations it was desirable to lengthen the pacemaker refractory period to insure that such retrograde depolarizations would not be detected. There was no device capable of determining the status of programmed refractory periods in respect to an ECG readout other than by doing extensive diagnostic interpretations of many ECG tapes.

In the past, there has not been any quick and easy method by which a physician could display cardiac events in conjunction with an ECG wave pattern, such that both were synchronized in time. Such display of the cardiac events over the portion of the ECG of the ECG wave pattern where it took place was not possible. Additionally, in situations where there were arrhythmias or other unnatural pacing problems, there were no devices capable of determining whether the events were truly what they appeared to be on the ECG wave pattern.

When this was the situation and the evaluation of the ECG tape was not in real time, the patient, if his pacing apparatus was not functioning properly, could possibly be injured because there was not a quick evaluation in real time of what was going on. Therefore, because of the physician's inability to conduct such real time evaluations on a visual display, there could not be an effective evaluation of the proper or improper functioning of the cardiac pacing apparatus that was implanted.

These and other problems are solved by the apparatus of this invention.

SUMMARY OF INVENTION

The present invention relates to an apparatus which is capable of receiving at least two sets of information signals, process the sets of information signals through a plurality of parallel processing channels, or equivalent, and display on a display surface visual representations of the two sets of information signals.

The sets of information signals that are processed are generally those which the apparatus receives telemetrically from an implanted heart pacing apparatus. These signals mark specific cardiac events as seen or generated by the pacing apparatus or specific operating states or conditions of the pacing apparatus. The cardiac events for which signals are telemetered from the pacing apparatus include a sensed P-wave, a sensed R-wave, a ventricular pulse output by the pacing apparatus, or an atrial pulse output by the pacing apparatus. Operating states or conditions for which signals may be telemetered include the mode of operation (e.g., VVI, DVI, etc.) of the pacemaker, the model number of the pacemaker, the duration of selected time periods used within the control circuits of the pacemaker (such as refractory time periods), and the like. The cardiac pacing apparatus outputs unique sets of telemetric signals for these different cardiac events or conditions, many of which are preferably transmitted and evaluated in real time in conjunction and in synchrony with other signals so as to enable a meaningful evaluation of the signals to be made. The signals output by the cardiac pacemaker are generally encoded digital signals.

These signals are received by an antenna means, which in the case of the present invention is a telemetry head. In accordance with one embodiment of the invention, the telemetry head preliminary processes the received signals in order to determine the type of signal received. A first set of signals is sent to a first signal interpreting means, a second set of signals is sent to a second signal interpreting means, and so on. Each signal interpreting means processes the signals received, and forwards them to a controller, where the signals may be further processed. The controller may also receive signal inputs from an additional interpreting means that is connected to an electrical conduit which has ECG electrodes disposed at the end. Each of the electrodes may be attached to the body of an individual. These electrodes take analog skin ECG readings of the individual having the heart pacing apparatus implanted therein. The analog signals from the ECG electrodes are received by the appropriate signal interpreting means, where they are initially processed (e.g., converted to a digital signal), and then forwarded to the controller for further processing.

The controller synchronizes, in real time, the sets of information signals received. Digital command signals resulting from this process are sent to a memory. The memory receives the addressed signals from the controller and outputs memory signals to a display logic portion of the apparatus. The display logic portion then processes the memory signals through logic gates and provides an output of display command signals. The display command signals are received by the display monitor having a display surface. Selected cardiac or pacemaker event conditions are then displayed simultaneously on the display surface in a synchronized manner in real time.

As indicated, the apparatus also receives and stores within its memory the refractory periods which are set for the implanted cardiac pacemaker (the programmed refractory period). Each time a cardiac event takes place, either a sensed P-wave, sensed R-wave, atrial pulse or ventricular pulse, the refractory period is displayed beneath the specific cardiac event in a linear fashion so that it well extend horizontally in real time in conjunction with the real time cardiac event and ECG wave pattern.

The cardiac pacing apparatus also outputs telemetric signals which mark the lengthening of the refractory periods of the pacing apparatus. These events are also processed by the apparatus and displayed on the display surface of the display monitor. The lengthened refractory periods of the pacemaker are displayed literally in a horizontal fashion as described above, adjacent to the programmed refractory period for the particular cardiac event.

Therefore, the present apparatus provides the diagnostic abilities not seen in any heretofore known apparatus. The present invention additionally has the ability to display the time periods between designated cardiac events. Such time periods could be between a P event and R event, R event and P event, or any other combination of events that are desired by the physician or other technical person. These display time periods can be used for determining such things as AV delay, retrograde transmission time, and other specifics of the heart activity.

An object of the invention is to provide an apparatus which has the ability to receive telemetric signals from an implanted cardiac pacing apparatus and provides a synchronized display representative of the signals received which are indicative of different cardiac events.

Another object of the invention is to provide an apparatus which has the ability to receive different sets of telemetric signals from a cardiac pacing apparatus for signifying specific cardiac events or pacemaker conditions, including selectively receiving signals from electrodes connected to the body of an individual, processing these sets of signals through parallel processing channels, and providing a display of the signals that is synchronized in the real time, the display therefore indicating the cardiac events, the pacemaker conditions, and/or the ECG wave pattern of an individual.

A further object of the invention is to provide an apparatus which displays in real time representative symbols indicative of the sequential cardiac events as determined by an implanted cardiac pacing apparatus.

A still further object of the invention is to provide an apparatus which synchronizes an ECG wave pattern with sequential cardiac events such that the cardiac events are displayed over the point along the ECG wave pattern where they take place.

Another object of the invention is to provide along with the real time representation of the cardiac events the time period between designated events.

Another object of the invention is to provide a display of the specific sequential cardiac events in real time over the ECG wave pattern which is synchronized with the cardiac events, the time period between the cardiac events and the refractory periods when both the lengthened refractory period and programmed refractory period for pacing apparatus are displayed.

A further object of the invention is to provide an apparatus that can receive a plurality of telemetry signals from an implanted cardiac pacing apparatus where such telemetry signals are indicative of cardiac events which are capable of being displayed in real time or timed by the cardiac pacing apparatus.

These and other objects of the invention will be described in complete detail in the subsequent portions of this description.

BEST MODE FOR CARRYING OUT THE INVENTION

The present invention is an apparatus which interprets and displays cardiac events, as determined by an implanted cardiac pacemaker. Additionally, if selected, the ECG wave pattern may be displayed in a synchronous manner on a display surface in real time with the information telemetered from the implanted pacemaker.

Figure 1A:
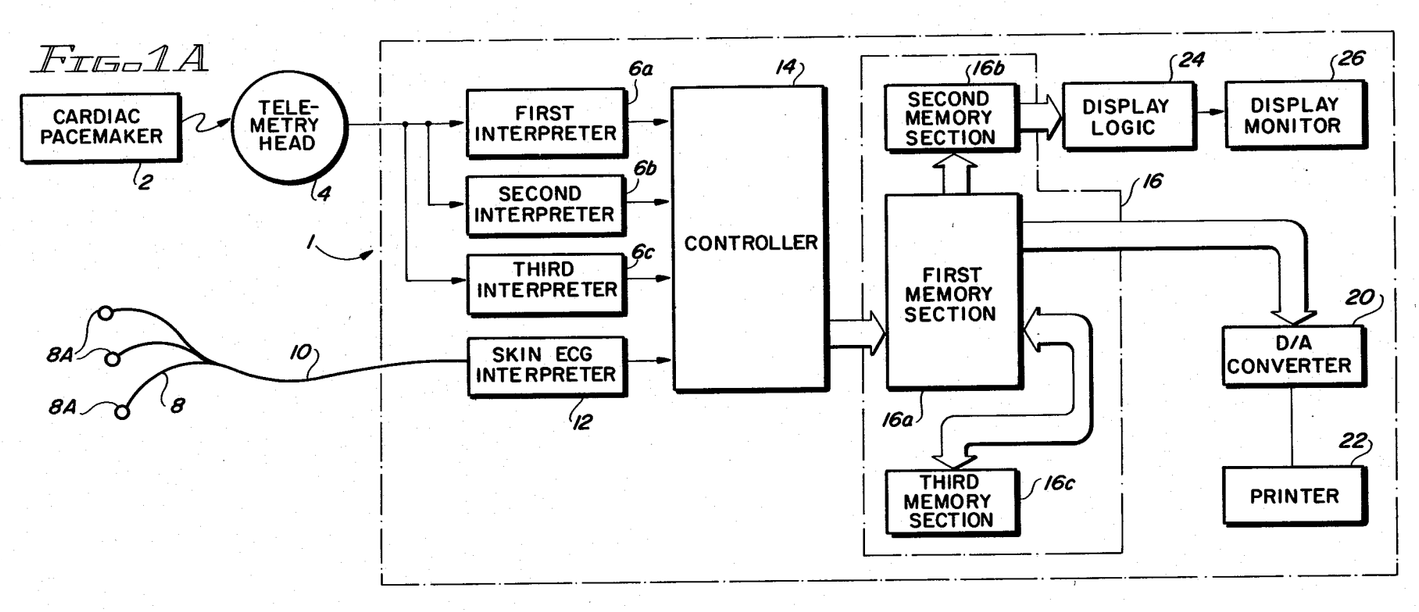
FIG. 1A shows a block diagram of one embodiment of the apparatus of the invention.

Referring to FIG. 1A, a block diagram of one embodiment of the apparatus of the invention is generally shown at 1. A telemetry head 4 and ECG electrodes 8, with supporting electrical conduit 10, are part of the apparatus of invention but are detachably fixed to it.

The cardiac pacemaker 2 is a conventional type of programmable pacemaker with the added features of transmitting unique telemetric signals for different cardiac events as determined by the cardiac pacing apparatus. The cardiac events for which telemetric signals are transmitted include sensed P or R-waves, atrial or ventricular pulses generated by the cardiac pacemaker, and the start and stop of the refractory period for the atrium or ventricle. Other status or sensed information from the pacemaker may also be transmitted.

The telemetric signals transmitted by pacemaker 2 for indicating different cardiac events and other information are received at telemetry head 4. The signals are RF signals. However, even though the primary method of transmitting the signals is by use of telemetry, any other conventional means can be used. These RF signals transmitted by cardiac pacemaker 2 are encoded digital signals which are interpreted and processed as will be described subsequently.

Figure 2A:
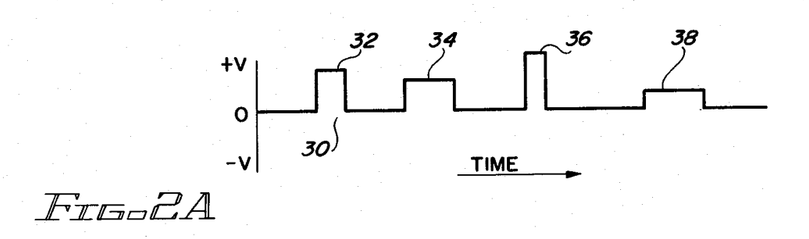
FIG. 2A shows one form of encoded signal received from the pacing apparatus for the different cardiac events which are telemetrically transmitted to the apparatus of the invention.

Referring momentarily to FIG. 2A, one representation of the wave forms for the signals transmitted by the cardiac pacemaker 2 in their decoded form is generally shown at 30. The square waves 32, 34, 36 and 38 all differ in some way. The pulses can vary in amplitude along, pluse width alone or amplitude and pulse width together. In the preferred embodiment of the invention, each of the RF pulse wave forms are unique in both amplitude and pulse width for each cardiac event.

Figure 2B:
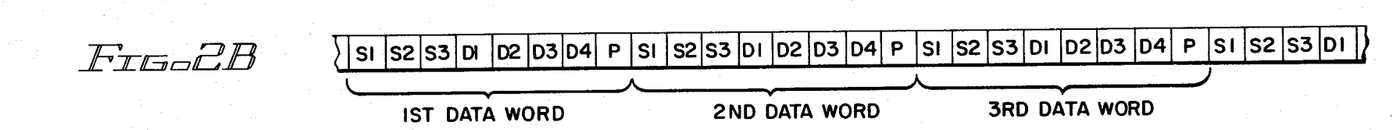
FIG. 2B shows another form of digital signal format representative of the sets of information received that indicate the different events or pacemaker conditions.

FIG. 2B shows an alternative representation of the decoded signals transmitted by the cardiac pacemaker 2. The signals in FIG. 2B comprise eight bit digital words, each word having three identification bits S1-S3, four data bits D1-D4, and a parity bit P. Any suitable form of modulation and encoding could be used to define these bits. Further, while 8 bits are shown in FIG. 2B, any number of bits could be used in any arrangement. Each digital word belongs to a certain data set, defined by the S1-S3 bits; and contains a unique data value, defined by the D1-D4 bits, for the cardiac event or other information of the data set being transmitted. Data sets may include atrial channel sensing, atrial channel stimulating, ventricular channel sensing, ventricular channel stimulating, atrial refractory period and ventricular refractory period.

Figure 2C:
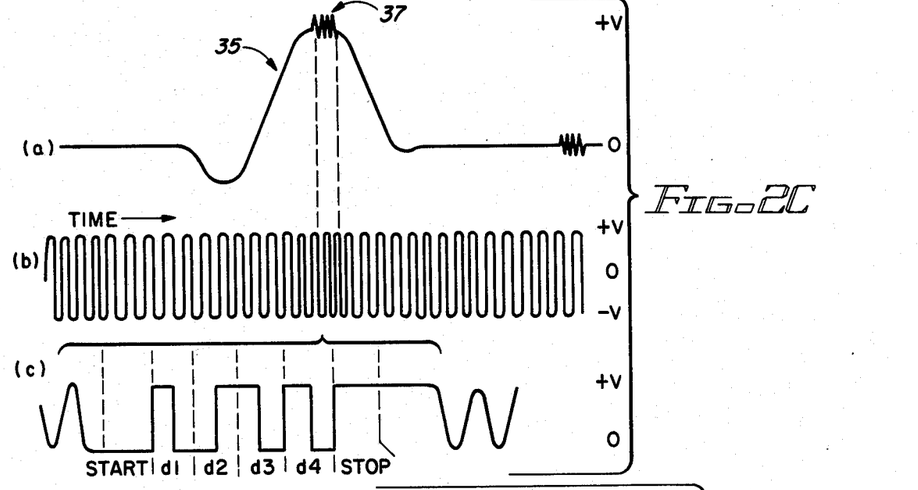
FIG. 2C is a timing diagram showing yet another manner in which data, both analog and digital, is telemetered to the apparatus of the invention.

FIG. 2C depicts another form of data signals that may be used to transmit desired information from inside the implanted pacemaker to the external apparatus of the present invention. In FIG. 2C, the upper waveform "a" represents an analog signal that is sensed by the pacemaker, such as an R-wave 35, and that is desired to be transmitted to the external apparatus 1. At the peak of the R-wave, a digital marker code 37 or identification signal is also desired to be sent. The analog signal is transmitted, in accordance with the embodiment shown in FIG. 2C, using an FM modulation scheme. The FM signal is depicted in the middle waveform "b" of FIG. 2C. This FM signal has a baseline or center frequency of, for example, 1800 Hz, and the FM signal can vary, for example, plus or minus 400 Hz about this center frequency depending upon the amplitude of the analog signal. At the point in time where the marker code 37 is to be transmitted, the FM signal is interrupted as shown in the expanded waveform "c" of FIG. 2C. This interruption includes a 6 bit digital word that is realized using a binary phase-encoded modulation scheme. In accordance with this encoding scheme, a start bit (easily detected because its period exceeds the longest possible period of the preceeding FM signal) indicates the beginning of a marker code. The next four bits, d1-d4 are data bits that define the particular marked code being transmitted. For example, such marked codes could represent the present state of the pacemaker logic circuits, from which state the identity of the analog signal being transmitted could be easily made. To illustrate, for the situation shown in FIG. 2C, the state of the pacemaker circuits (as represented by the marker code), might indicate an R-wave alert state. Thus, the analog signal being transmitted would have to be a signal sensed in the ventricle of the heart, i.e., an R-wave. Other codes are used to represent other states of the pacemaker, such as atrial or ventricular refractory states, an atrial alert state, or atrial or ventricular pacing states. After the four data bits, a stop bit indicates that the code is completed, and the FM signal resumes.

Referring back to FIG. 1A, the first signal interpreter 6a receives the encoded RF pulses from telemetry head 4, corresponding to a particular data set or type, interprets (or decodes) these signals initially and then processes the signals in accordance with the specific type of cardiac event or data set the signal represents. Similarly, the second and third signal interpreters 6b and 6c receive the encoded signals of respective data sets or types, and process these signals accordingly. For example, signal interpreter 6a may receive and preliminarily process atrial channel signals (paced or sensed signals in the atrium); signal interpreter 6b may receive and preliminarily process ventricular channel signals, and signal interpreter 6c may receive and preliminarily process other sensed or status signal. In general, these interpreters 6a, 6b and 6c can be relatively simple because cardiac events take place sequentially; therefore, they need only interpret one pulse (or signal or word) at any given point in time. The further processing of the signal after interpretation by the appropriate signal interpreter 6a, 6b or 6c comprises preparing the signals as an information signal input for controller 14.

The electrodes 8 comprise a plurality conventional ECG electrodes with paddles 8a attached to the distal end of each. The paddles 8a are attached to the skin of the individual in the normal manner for taking a skin ECG. When such attachment of paddles 8a take place, electrical signals (analog) are received from paddles 8a and transmitted to electrodes 8. These signals are transmitted through electrical conduit 10 to skin ECG signal interpreter 12. The fourth signal interpreter 12 receives the analog input, processes it and provides a digital output which comprises an additional information signal input for controller 14.

Controller 14 receives the informational signals from the signal interpreters 6a, 6b, 6c and 12. The controller 14 has a variety of functions. One of its main functions is that it synchronizes the input signals in time, and processes them in a parallel manner.

The controller 14 also serves as a communications sequencer and addressing means for the digital inputs received from the various signal interpreters 6a, 6b, 6c and 12.

To perform these functions, the controller 14 takes the inputs, synchronizes them, and after such synchronization puts certain information on a data bus for memory 16 and provides certain command signals for addressing the data in the bus in memory 16. A majority of this data processing takes place automatically but there are some external commands that are input to controller 14 manually. The command signals which are externally controlled are the "Freeze" command and the "Expand" command which will be described subsequently.

Figure 1B:
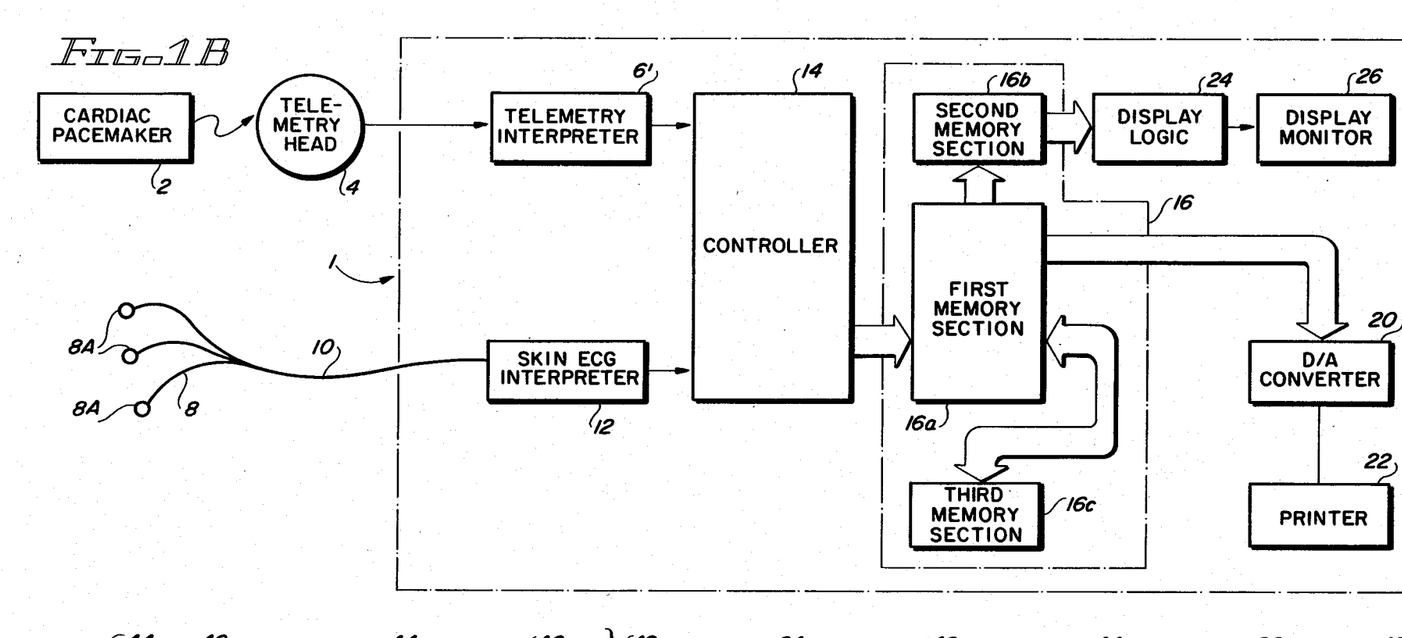
FIG. 1B shows a block diagram of an alternative embodiment of the apparatus of the invention.

Referring next to FIG. 1B, an alternative embodiment of the apparatus is shown. The embodiment of FIG. 1B differs from the embodiment of FIG. 1A in that only two signal interpreters, a telemetry interpreter 6' and a skin ECG interpreter 12, are employed. The skin ECG interpreter 12 of FIG. 1B is the same as in FIG. 1A. The telemetry interpreter 6' of FIG. 1B is substantially the same as the signal interpreters 6a, 6b and 6c of FIG. 1A, except that all of the telemetry signals received by the telemetry head 4 pass therethrough. Thus, in effect, there is a single signal channel (of which the telemetry interpreter 6' is a part) that couples the telemetry head 4 with the controller 14. However, because the data passing through this channel belongs to identifiable data sets, each data set can effectively be processed in the controller 14 as though the data were received over parallel channels. Hence, so long as the telemetered data sets are uniquely identifiable (and therefore capable of being separated and processed in parallel at the controller), the embodiment of FIG. 1B is essentially functionally equivalent to that of FIG. 1A. Each embodiment allows the synchronization between the data sets to be maintained as the data is processed.

Controller 14 provides the data and command outputs for three part memory 16. The first memory section, 16a, contains the software program information for controlling the apparatus. The second memory section, 16b, contains the information for controlling the hardware of the display monitor 26. The third memory section, 16c, is a non-volatile memory which contains additional memory for storing information which can be recalled at a later time. Memory section 16c is primarily used for recordation of data so that a physician or other technician can recall historical data on the patient when desired.

The connections between the memory sections 16a, 16b and 16c in the primary embodiment are as indicated in FIG. 1. The connection between the first section 16a and second section 16b is a unidirectional connection (from 16a to 16b). The connection between 16a and 16c is bidirectional so that retrieval of stored information can be accomplished. This could also be accomplished using one large memory or a series of small memories and still fall within the intended scope of the present invention.

First memory section 16a has one output that connects to digital to analog (D/A) convertor 20. The D/A convertor 20 changes the digital output of Section 16a to an analog output for driving a printer 22. The use of this portion of the apparatus is primarily for printing out historical data on the patient stored in third memory section 16c.

While the invention uses D/A converter 20 and printer 22, the inventors also contemplate the use of a visual display surface having logic means disposed between it and the memory which is responsive to the digital signal output by the memory. Therefore, when this visual display surface is used, there is no absolute need for D/A convertor 20. The D/A convertor is necessary if a supplementally printer is attached to the display surface in order to produce a hard copy of the historical information retrieved from memory 16c.

As previously stated, first memory section 16a provides a unidirectional output to second memory section 16b. The second memory section 16b contains in memory the information for controlling the display monitor 26. The signals from section 16a access section 16b causing a digital output from 16b to display logic portion 24.

The display logic portion 24 receives the output of memory section 16b and through a series of logic gates provides a digital output to display monitor 26. The output signals from memory section 16b to display logic 24 are the synchronized signals processed by controller 14 and received through the first, second and third signal interpreters 6a, 6b, 6c, and the skin ECG interpreter 12 of FIG. 1A, or through the telemetry interpreter 6' and skin ECG interpreter 12 of FIG. 1B.

The output of display logic portion 24 drives display monitor 26 which has a display surface (or screen). The signals output by display logic portion 24 which drive display monitor 26 are processed by display monitor 26 is such a manner that each cardiac event will be represented by a unique character or symbol on the display surface. These cardiac events are also displayed sequentially in real time as they take place. The unique characters are displayed first at a first side of the surface and appear sequentially in time across the surface until they reach a second side of the display surface. When they reach the second side of the display surface they will switch back to the first side of the surface and repeat this procedure during the period telemetry signals are being received by the apparatus.

Figure 5:
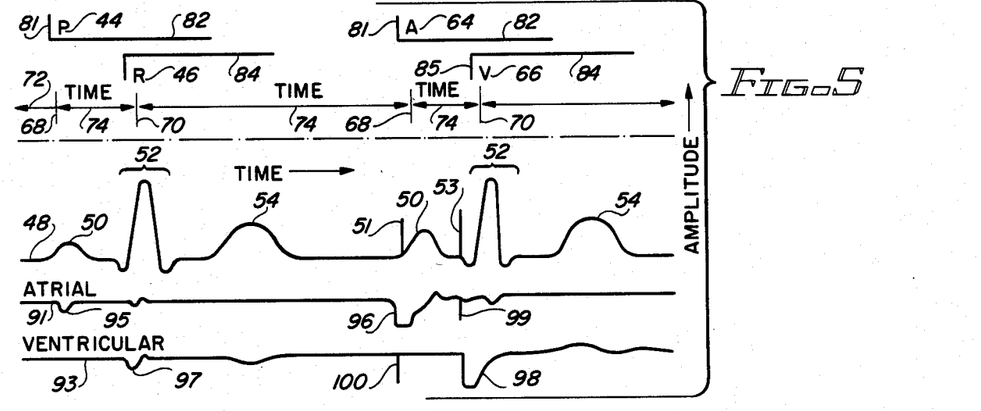
FIG. 5 shows the type of waveforms that may be displayed on the display surface of the apparatus of invention, which display includes intracardiac ECG information as well as skin electrode ECG information.
Figure 6:
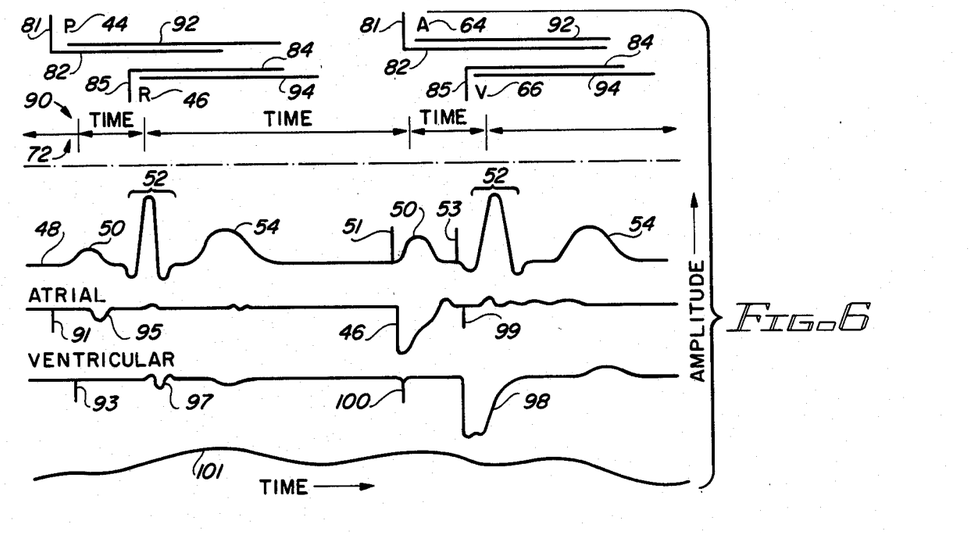
FIG. 6 also shows the type of waveforms that may be displayed as in FIG. 5, which display includes implanted sensor information.

Advantageously, a plurality of synchronized data sets or information may be displayed simultaneously on the display monitor 26. In the preferred embodiment, intracardiac ECG signals (that is, signals sensed within the pacemaker and telemetered to telemetry head 4) as sensed in either the atrium and/or the ventricle of the heart may be displayed. Skin ECG signals as sensed through skin electrodes 8 may also be displayed along with these telemetered intracardiac ECG wave forms. Examples of such comprehensive displays are depicted in FIGS. 5 and 6. Timing information, refractory time periods, or other sensed or status information, may also be displayed as shown in these Figures and as discussed below.

The ECG signals received and output by the skin ECG interpreter 12, or the telemetered intracardiac ECG signals for the atrium and/or ventricle, are displayed on the display surface spaced apart and beneath but synchronized with visual representations of the cardiac event being displayed.

The skin ECG wave pattern is a continuous wave pattern showing the P-wave, QRS complex and T-wave consistent wth a normal ECG wave pattern. This wave pattern, when selected for dsplay, shows the actual ECG pattern for the person connected to paddles 8a.

The wave pattern, like the cardiac event, begins at the first side on the surface but is displayed continuously as it takes place in time until it reaches a second side of the surface. When the wave pattern reaches the second side of the surface it switches back to the first side to continue the wave pattern. This will continue as long as the person is connected to paddles 8a of electrodes 8.

The remaining figures, namely FIGS. 3 through 6, represent the types of signal waveforms, which may be shown on the display surface (or screen) of display monitor 26.

Figure 3:
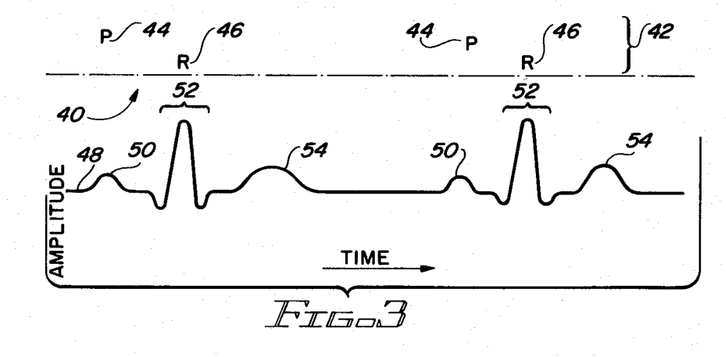
FIG. 3 shows one embodiment of the display for the display surface of the apparatus of invention.

Referring to FIG. 3, the basic visual representation of the telemetric signal received from cardiac pacing apparatus 2, indicative of cardiac events, and skin ECG signals, indicative of the skin ECG of an individual, are shown generally at 40. This is the representation that is shown in the display surface. The cardiac events are shown sequentially in time as 44 and 46 representing P-waves and R-waves, repectively. Skin ECG pattern 48 is shown spaced away and below the representation for the cardiac events.

The cardiac events at 44 and 46, and skin ECG pattern at 48 and 52, are synchronized in time. The wave displacements from the base line of the continuous ECG pattern which represent specific cardiac events have shown above them a unique cardiac event symbol. The unique cardiac event symbols are a "P" to represent a sensed P-wave, and "R" to represent a sensed R-wave, and "A" to represent an atrial pulse output by the cardiac pacing apparatus 2 to depolarize the atrium, or a "V" to represent a ventricular pulse output by cardiac pacing apparatus 2 to depolarize the ventricle. The P or A symbols are displayed in a position slightly higher than the R or V symbols as a symbolic representation that the atrium is the upper portion and the ventricle is the lower portion of a heart.

The physician or technician, as desired, can display either the sequential cardiac events 44 or 46 alone, skin ECG wave pattern 48 alone, atrial intracardiac waveform 91 alone, ventricular intracardiac waveform 93 alone, patient sensed information 101 alone, or various combinations of these waveforms and events simultaneously. While the paragraphs hereafter are generally directed to the simultaneous display of the synchronized visual outputs of the cardiac events and skin or intracardiac ECG wave patterns, singular representations are also contemplated.

Referring again to FIG. 3, when the cardiac pacing apparatus 2 senses a P-wave, and a unique telemetric signal is output indicative of it, the representative symbol "P", 44, is displayed on the display surface. The continuous ECG wave pattern 48 will indicate P-wave 50 beneath the cardiac event symbol 44. As time progresses, the next sequential cardiac event, in a normal heart operating with pacing apparatus 2, is an R-wave. The representative symbol "R", 46, for the R-wave is displayed on the display surface. Beneath the symbol 46, the ECG wave pattern that is synchronized with the cardiac event, displays QRS complex 52 which is representative of the R-wave. The ECG wave pattern 48 also will show T-wave 54 when sensed on the electrodes 8. However, the T-wave does not show up as a cardiac event. Although, if desired, there could be a representation of a T-wave on cardiac events line 48, it is usually masked by the refractory periods of the chambers. There are no remaining cardiac events shown on the ECG wave pattern 48 for the remainder of the heart cycle. After the cycle is completed, the foregoing is repeated, with the cardiac events and the ECG wave pattern (if selected) being displayed.

When there is not a natural depolarization of the atrium or ventricle, the pacing apparatus 2 will put out an electrical pulse to depolarize the chamber tissue that did not naturally depolarize. When this takes place, the representation symbol "A" (64 of FIG. 4) is displayed on the display surface. If a ventricular pulse is put out by the cardiac pacing apparatus 2, the representation symbol "V" (66 of FIG. 4) is displayed on the display screen. The symbols "A" and "V" are displayed over P-wave 50 and QRS complex 52 of the ECG wave pattern 48 because it is the "A" or "V" pulses that cause the depolarization of the respective chambers and cause the ECG wave deflection 50 and 52. Additionally, when the A or V pulses are output to cause depolarization, the electrodes 8 will be responsive to the output and spikes 51 and 53 will be displayed on the display surface which are indicative of such output pulse.

In situations when the patient is experiencing a tachycardia of the atrium or ventricle, the actual sequence of depolarization will be shown on both the cardiac events line 42 and the ECG wave pattern 48. The method of using the displayed information to break such tachycardias will subsequently be described. However, whatever type of tachycardia takes place, there will be representative symbols for the cardiac events and the ECG pattern 48.

Figure 4:
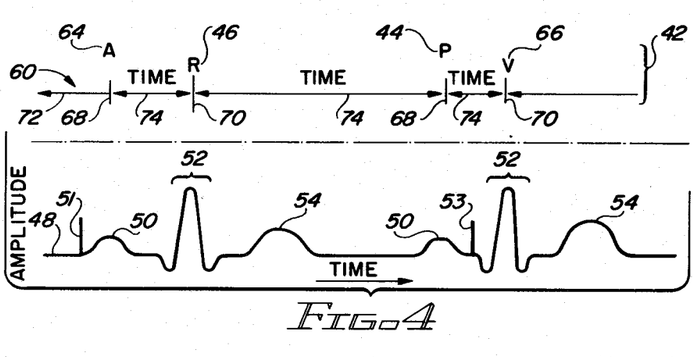
FIG. 4 shows another embodiment of the display for the display surface of the apparatus of invention.

Referring to FIG. 4, a second embodiment of the visual display is shown generally at 60. As in FIG. 3, the cardiac events are displayed on the cardiac events line 42 and the ECG wave pattern is displayed at 48. The cardiac events line 42 shows the representation symbols "A", 64, and "V", 66, for an atrial or ventricular pulse put out by the pacing apparatus 2, respectively. This secondary embodiment of the display has added thereto vertical indicators or markers 68 and 70 to indcate the specific point of depolarization of the atrium or ventricle caused by a natural P-wave or atrial pulse from pacing apparatus 2; or natural R-wave or ventricular pulse from the pacing apparatus 2, respectively. In this embodiment, the indicators 68 and 70 are of different lengths, so at a glance it can be determined whether the cardiac event along the ECG wave pattern is from the group "P" or "A"; or the group "R" or "V".

Additionally, the apparatus has the ability to display the elapsed time between any two cardiac events. Therefore, the time intervals shown as "Time" at 74 will be displayed on the display surface in the indicated positions as numerals representing the length of the time interval. Although the time period 74, as shown in FIG. 4 is only for that time between consecutive events, there can be time periods displayed between any two events whether consecutive or not.

Referring to FIG. 5, a third embodiment of the display is shown generally at 80. This embodiment displays what was displayed in the embodiments of FIGS. 3 and 4 with the addition of horizontal indicator 82 and 84 and atrial and ventricular intercardiac waveforms 91 and 93. The horizontal indicators 82 and 84, in real time, indicate the programmed and/or actual refractory periods of the atrium and ventricle as set or measured by pacing apparatus 2. The horizontal indicator extends from the cardiac event to the end of the respective refractory period. The atrial refractory period has vertical section 81 which extends upward from horizontal line 82. The ventricular refractory period has vertical section 85 which extends down from horizontal line 84. This proves to be helpful information in determining whether the pacing apparatus 2 has been programmed with the proper refractory period. If the T-wave is not totally enclosed in the refractory period of the "P" or "A" it could cause another depolarization of the atrium. Therefore by viewing the display, it will indicate if the refractory period is too short for the characteristics of a particular heart.

The atrial intracardiac waveform 91 of FIG. 6 includes an indication of natural atrial depolarization (sinus P-wave) 95, and paced or stimulated atrial depolarization (paced P-wave) 96. Also included is a far-field V-pulse 99. (The "V-pulse" is the pulse used to stimulate the ventricle. Because it occurs in a different chamber of the heart from the one being sensed, it is termed "far-field". The ventricular intracardiac waveform 93 includes an indication of natural ventricular depolarizaton (QRS complex) 97, paced ventricular depolarizaton (paced R-Wave) 98, and far-field A-pulse 100.

Referring now to FIG. 6, a fourth embodiment of the display is shown generally at 90. This embodiment has all of the features of the foregoing three embodiments with the added features of horizontal indicators 92 and 94, which indicate the actual refractory period of the pacemaker. The actual and programmed refractory periods of the pacemaker are the same except in cases when there is noise on the P or R sensing channels of the pacing apparatus 2. In such cases there is a lengthening of the programmed refractory period and the actual and programmed refractory periods are different. In such cases, the lengthened period will be displayed as 92 or 94.

Also included in FIG. 6 is a sensor signal 101. This signal may be selectively displayed whenever a physiological sensor of some sort is employed by the pacemaker. Such a physilogical sensor might sense the patient's physical activity, blood-oxygen content, respiration rate, or other physilogical parameters. In general, this signal will be a slowly varying analog signal. Because it varies slowly relative to a few cardiac cycles, however, other forms of display could be used, such as a number display wherein an average value or changed value of the physiological parameter is displayed.

In situations in which a patient has continued problems with tachycardias, the apparatus of the invention can be used to determine when the pulse should be delivered to break the tachycardia. The apparatus displays the period of time it takes to cause a depolarization in the atrium after a depolarization in the ventricle. This time period is the retrograde transmission time. The displayed time period will give the retrograde V-A delay. From this a physician can determine how to make the proper setting for the anti-tachycardia modes of the pacing apparatus 2 to break and prevent tachycardias. Likewise, in situations in which there is a tachycardia in the antegrade direction, the point of breaking the tachycardia can be ascertained by determining the A-V delay, from which the best time to apply a stimulating pulse to the realize ventricular capture can be found.

The apparatus has means, which when activated will cause the current display to be "frozen" and "expanded" for high resolution of a particular visual display. This can also be done for information retrieved from memory 16c. This frozen and expanded display can then be printed out on the printer 22 or display monitor 26.

Although the timed or cardiac events for which representative symbols or timing lines are displayed were for sensed P or R-waves, atrial or ventricular pulses output by the pacing apparatus, and programmed or actual refractory periods, there are other timed events or cardiac events which can be displayed on the display surface as long as a telemetric signal marking the cardiac event or timed event is output by the pacing apparatus. Additionally, even though the preceding paragraphs state that the display surface displays cardiac events and ECG wave pattern, there is also the ability of the apparatus to display other visual forms such as a ladder diagram or other similar figures. These figures will also be synchronized in real time with the figures represented on the display surface.

The terms and expressions which are employed here are used as terms of description and not of limitation and there is no intention, in the use of such terms and expressions, of excluding equivalents of the features shown, and described, or portions thereof, it being recognized that various modifications are possible in the scope of the invention as claimed.

What is claimed is:

1. An apparatus for displaying cardiac events of a heart connected to an implanted cardiac pacemaker of a patient, said apparatus comprising:

first receiving means for receiving a first set of telemetered information from said implanted pacemaker;

second receiving means for receiving a second set of telemetered information from said implanted pacemaker;

controller means coupled to said first and second receiving means for synchronizing in time the telemetered information received through said first and second receiving means, and for processing the information thus received in parallel while maintaining the synchronization therebetween, said controller means generating digital command signals representative of the information received through the first and second receiving means and the synchronization therebetween;

memory means for storing said digital command signals; and display means responsive to said digital command signals stored in said memory means for simultaneously displaying a synchronized representation of the telemetered information received through the first and second receiving means.

2. The apparatus of of claim 1 wherein said first receiving means comprises telemetry head means for receiving telemetered information from said implanted pacemaker coupled to said controller means via a first information channel; and wherein said second receiving means comprises said telemetry head means coupled to said controller means via a second information channel.

3. The apparatus of claim 1 further including third receiving means for receiving a third set of information from skin electrodes placed at the skin of said patient, said third set of information being separate and distinct from the first and second sets of information received through said first and second receiving means.

4. An apparatus for displaying cardiac events of a heart connected to an implanted cardiac pacemaker of a patient, said apparatus comprising:

telemetry head means for receiving telemetered information from said implanted pacemaker;

controller means coupled to said telemetry head means via channel means for synchronizing in time the telemetered information received over the channel means, and for processing a plurality of sets of information contained within said telemetered information in parallel while maintaining the synchronization therebetween, said controller means generating command signals representative of the information contained in each of said sets of information and the synchronization therebetween;

said channel means including means for transferring to said controller means from said telemetry head means each of said plurality of sets of information in a way that maintains the identity of each set of information, each set of information including information relating to the pacemaker and events sensed by the pacemaker;

memory means for storing said command signals; and display means responsive to said command signals stored in said memory means for simultaneously displaying a synchronized representation of the information derived from a selected plurality of said sets of information received through said telemetry head means and said channel means.

5. The apparatus of claim 4 wherein a first set of said plurality of sets of information contains cardiac event information sensed within said heart, and a second set of said plurality of sets of information contains pacemaker status information relating to the operation of said implanted cardiac pacemaker.

6. The apparatus of claim 5 wherein said first set of information contains cardiac event information sensed within the atrium of said heart, and wherein a third set of information contains cardiac event information sensed within the ventricle of said heart.

7. The apparatus of claim 4 further including means for receiving skin ECG information within said controller means as a separate set of information, said skin ECG information being processed in parallel with the received sets of telemetered information while maintaining the synchronization between the skin ECG information and the telemetered information.

8. In combination with an implanted cardiac pacemaker having telemetry means for telemetering data sensed and measured by said pacemaker, an apparatus for displaying a plurality of cardiac events in synchronization, said apparatus comprising telemetry head means for receiving said telemetered data;

processing means for processing said received telemetered data, said processing means including means for separating said telemetered data into a plurality of sets of data, each set of data relating to a specific cardiac/pacemaker event, at least one of said plurality of sets of data representing specific cardiac/pacemaker events that are sensed by said pacemaker, and another of said plurality of sets of data representing marker information that identifies the type of cardiac/pacemaker event that has been sensed and the time at which said event was sensed, means for interpreting and processing said sets of data while maintaining the synchronization therebetween, means for generating command signals representative of the synchronization between said sets of data, and memory means for storing said processed sets of data and said command signals; and display means coupled to said processing means for selectively displaying a synchronized representation of the information contained in a plurality of said sets of data, said display means including means for displaying said sensed cardiac/pacemaker event in a way that the display is marked with said marker information so that the display apparatus identifies the type of cardiac/pacemaker event that occurred and the time at which it occurred.

9. The display apparatus of claim 8 wherein said marker information includes information relating to the beginning of a refractory period initiated by said pacemaker.

10. The display apparatus of claim 8 wherein said processing means further includes means for receiving a set of data relating to skin ECG data, said skin ECG data comprising data sensed at the skin of a patient that is not telemetered through said telemetry head means, and wherein the data separating means of said processing means separates said skin ECG data into an identifiable set of data while maintaining the synchronization between said skin ECG data and said plurality of sets of telemetered data.

11. An apparatus for displaying cardiac/pacemaker events of a heart in communication with a cardiac pacemaker, said pacemaker including means for sensing and monitoring a plurality of cardiac/pacemaker events and telemetering respective data signals representative of the occurrence of said cardiac/pacemaker events, said apparatus comprising:

means for receiving said data signals;

means for processing said data signals in parallel in a plurality of data channels, said means for processing including means for classifying said data signals as belonging to one of a plurality of specified data sets, means for directing the data signals of each data set to a respective data channel, and means for maintaining the synchrony or timed relationship between the data signals of each data set within each data channel as said data signals are processed for display;

means for displaying a selected plurality of said data signals in a single multi-channel time-base display;

said means for displaying including:

a display surface, means for displaying on said display surface a plurality of display channels having elapsed time as one axis thereof, and means for displaying in each of said display channels a representation of selected data signals from a specified data set, each such representation depicting the occurrence of a corresponding cardiac/pacemaker event as a function of time, the combined display channels thereby depicting a selected plurality of cardiac/pacemaker events as a function of time, whereby a synchronized display of said selected plurality of cardiac/pacemaker events is realized.

12. The apparatus of claim 11 wherein a fourth of said data sets comprises data signals representing a sensed physiological parameter of a patient in whom said cardiac pacemaker is carried.

13. The apparatus of claim 11 wherein a first of said data sets comprises data signals representing sensed intracardiac ECG activity, and a second of said data sets comprises data signals identifying specific events, such as the sensing of a P-wave, included in the first data set.

14. The apparatus of claim 13 wherein a third data set comprises data signals representing specified time intervals associated with the operation of said pacemaker.

15. A method of displaying cardiac/pacemaker events of a heart controlled by an implanted cardiac pacemaker, said pacemaker including means for sensing and monitoring a plurality of cardiac/pacemaker events and telemetering respective data signals depicting the occurrence of said cardiac/pacemaker signals to an external, non-implanted receiving apparatus, said receiving apparatus including display means for displaying a plurality of data channels in a synchronized display, said method comprising the steps of:
   (1) separating the received data signals into a plurality of data sets, each data set containing data signals relating to a specific cardiac/pacemaker function,
   (2) processing the data sets in parallel processing channels, said processing in each channel including:
      (a) generating command signals identifying the sequence and timed relationship of the information contained in said data sets, said sequence and timed relationship of a given data set including the time when a particular data signal was received, the duration of said particular data signal, and the length of time between specified data signals within the same data set, and
      (b) storing said data sets and command signals for subsequent retrieval;
   (3) selectively presenting a plurality of data sets with respective command signals to said display means; and
   (4) displaying, in each data channel of said synchronized display, under control of said command signals, a selected one of said plurality of data sets, the events represented by said data sets being displayed in a sequence and timed relationship representative of the sequence and timed relationship of the information derived from the received data signals.

16. A method of externally identifying the types of signals sensed by an implanted medical device, said implanted medical device having transmitting means for sending to a non-implanted monitoring device the signals sensed internally by the implanted medical device, said method comprising the steps of:
   (1) transmitting the sensed signals of the implanted medical device to the non-implanted monitoring device;
   (2) transmitting, in conjunction with each transmitted signal sent in step (1), a marker code signal that identifies the sensed signal that has been transmitted;
   (3) processing the signals transmitted in steps (1) and (2) within said non-implanted monitoring device in order to prepare such signals for display; and
   (4) displaying the sensed signal and its associated marker code signal on a multi-channel display surface of the non-implanted monitoring device, said step of displaying including:
      (a) presenting the sensed signal on a first display channel of said display surface, said first display channel having a desired parameter, such as amplitude, as one axis thereof, and having time as another axis thereof, whereby the sensed signal is displayed as a function of time, and
      (b) presenting the marker code signal on a signal display channel of said display surface, said marker code signal being presented as an identifiable symbol that is displayed in synchrony with the sensed signal displayed on the first display channel, each component of interest of the displayed sensed signal being marked with an appropriate marker code that identifies that component of sensed signal.

17. The signal identification method of claim 16 wherein the implanted medical device comprises a pacemaker coupled to a heart and wherein the sensed signals comprise a first signal representing activity sensed in the atrium of the heart and a second signal representing activity sensed in the ventricle of the heart, and wherein step (4) (a) includes presenting the first signal on the first display channel of the display surface and presenting the second signal on a third display channel of the display surface, whereby both said first and second sensed signals are displayed as a function of time.

* * * * *